(12) United States Patent
Moberg et al.

(10) Patent No.: US 7,704,227 B2
(45) Date of Patent: Apr. 27, 2010

(54) METHODS AND APPARATUSES FOR DETECTING MEDICAL DEVICE ACCELERATION, TEMPERATURE, AND HUMIDITY CONDITIONS

(75) Inventors: Sheldon B. Moberg, Thousand Oaks, CA (US); Ian B. Hanson, Northridge, CA (US); Cary D. Talbot, Santa Clarita, CA (US); Jeffrey Ireland, Thousand Oaks, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 500 days.

(21) Appl. No.: 11/606,589

(22) Filed: Nov. 29, 2006

(65) Prior Publication Data

US 2008/0125701 A1 May 29, 2008

(51) Int. Cl.
*A61M 31/00* (2006.01)
*A61M 37/00* (2006.01)
*A61M 1/00* (2006.01)
*F04B 49/00* (2006.01)

(52) U.S. Cl. .................. 604/65; 604/131; 604/151; 417/18; 417/46

(58) Field of Classification Search ............ 604/65–67, 604/131, 151; 417/18, 46
See application file for complete search history.

(56) References Cited

U.S. PATENT DOCUMENTS

| 3,524,031 | A | * | 8/1970 | Mack ................ 200/61.53 |
| 5,408,878 | A | * | 4/1995 | Lysen ................ 73/514.34 |
| 6,477,421 | B1 | * | 11/2002 | Andersen et al. ......... 607/19 |
| 2001/0034502 | A1 | | 10/2001 | Moberg et al. |
| 2002/0042596 | A1 | | 4/2002 | Hartlaub et al. |
| 2002/0171297 | A1 | | 11/2002 | Talbot et al. |
| 2004/0176720 | A1 | | 9/2004 | Kipfer |
| 2005/0038332 | A1 | * | 2/2005 | Saidara et al. ........... 600/347 |
| 2005/0043676 | A1 | | 2/2005 | Remde et al. |
| 2005/0177137 | A1 | | 8/2005 | Kipfer |

FOREIGN PATENT DOCUMENTS

| FR | 2792841 A1 | 11/2000 |
| FR | 2880810 A1 | 7/2006 |
| JP | 11137673 | 5/1999 |
| WO | 02053223 A2 | 7/2002 |
| WO | 02053223 A3 | 7/2002 |
| WO | 2006075016 A1 | 7/2006 |
| WO | 2007138154 A1 | 12/2007 |

OTHER PUBLICATIONS

PCT International Search Report and Written Opinion for International Application No. PCT/US2007/085644 (dated Oct. 10, 2008).

* cited by examiner

*Primary Examiner*—Nicholas D Lucchesi
*Assistant Examiner*—Rebecca E Eisenberg
(74) *Attorney, Agent, or Firm*—Medtronic MiniMed, Inc.

(57) ABSTRACT

An ambulatory medical device for detecting acceleration, temperature, and/or humidity conditions in or around the medical device is provided. The medical device includes one or more acceleration, thermal, and/or humidity sensors which detect acceleration, temperature, and/or humidity conditions in or around the medical device. In response to detected conditions, the medical device may, among other things, alter the operation of the device, provide an alarm or warning to the user, or transmit data about the detected conditions to another device.

34 Claims, 5 Drawing Sheets

METHODS AND APPARATUSES FOR DETECTING MEDICAL DEVICE ACCELERATION, TEMPERATURE, AND HUMIDITY CONDITIONS

FIELD OF THE INVENTION

This invention relates generally to improvements in ambulatory medical devices, such as drug delivery systems or patient monitoring systems, and more specifically, to improved methods and apparatuses for detecting acceleration, temperature and humidity conditions in or around these ambulatory medical devices.

BACKGROUND OF THE INVENTION

Ambulatory medical devices, such as drug delivery systems and patient monitoring systems, are used in the therapy of various diseases or medical disorders, such as diabetes mellitus, pulmonary hypertension, thalassemia, and chronic pain. Many such devices are adapted to be carried by the user, for example, by means of a belt clip or harness, in the user's clothing pocket, or attached to the user's body or clothing.

A common drug delivery system includes a tubing arrangement to deliver medication to a user cutaneously or subcutaneously. For example, ambulatory infusion pumps are used in delivering a prescribed medication, such as insulin, to a user. In one form, these devices comprise a relatively compact pump housing adapted to receive a syringe or reservoir carrying a prescribed medication for administration to the user through infusion tubing and an associated catheter or infusion set.

The external infusion pump may include a small drive motor connected via a suitable transmission assembly for motor-driven advancement of a reservoir piston to administer the medication to the user. Programmable controls can operate the drive motor continuously or at periodic intervals to obtain a closely controlled and accurate delivery of the medication over an extended period of time. Such infusion pumps are used to administer insulin and other medications, with exemplary pump constructions and systems being shown and described in U.S. Pat. Nos. 4,562,751; 4,678,408; 4,685,903; 5,080,653; 5,097,122; 6,248,093; 6,362,591; 6,554,798; and 6,555,986, which are incorporated by reference herein.

External infusion pumps of the general type described above have provided significant advantages and benefits with respect to accurate delivery of medication or other fluids over an extended period of time. The infusion pump can be designed to be extremely compact as well as water resistant, and may be carried by the user, for example, by means of a belt clip or harness, in the user's clothing pocket, or attached to the user's body or clothing. As a result, important medication can be delivered to the user with precision and in an automated manner, without significant restriction on the user's mobility or lifestyle, including in some cases the ability to participate in water sports.

Due to their small size and portability, ambulatory medical devices can be subjected to a number of external conditions that may adversely affect their performance. For example, external infusion pumps can sustain an occlusion in the delivery tubing. Some pumps have alarm systems designed to detect and indicate pump malfunction or nondelivery of the medication as a result of occlusions. There exists, nevertheless, a need for further improvements in these ambulatory medical devices, particularly with respect to providing warnings or system operational changes in response to external conditions that may affect medical device performance.

BRIEF SUMMARY OF THE INVENTION

Disclosed are ambulatory medical devices that are adapted for carrying by a person on an exterior of the person's body, and include acceleration, thermal, and/or humidity sensors for detecting conditions in or around the devices. In response to the detected conditions, the medical devices may, among other things, alter the operation of the devices, provide alarms or warnings to the user, or transmit data to another device.

In one embodiment of the present invention, an ambulatory medical device such as an external infusion device for infusing fluid into a person from a reservoir comprises a housing adapted to be carried on an exterior of the person's body. The infusion device also includes a drive mechanism contained in the housing and operatively coupled to the reservoir to deliver the fluid from the reservoir into the person's body. The infusion device further includes a processor contained in the housing, and an indicator operatively coupled to the processor and adapted to indicate information about the infusion device to the person. An acceleration sensor also is coupled to the processor and is adapted to provide an acceleration output signal as a function of acceleration forces acting on the housing. The processor is adapted to control the infusion device in accordance with the acceleration output signal.

In particular embodiments, the infusion device further includes a memory contained in the housing and coupled to the processor. The memory is adapted to store a predetermined acceleration threshold corresponding to an impact on the housing. If the acceleration output signal exceeds the predetermined acceleration threshold, the processor is adapted to control the infusion device by causing the indicator to provide an alarm or a warning to the person about the impact. Alternatively, the processor is adapted to control the infusion device by causing the drive mechanism to alter delivery of the fluid into the person's body. In further alternative embodiments, the infusion device also includes a transmitter/receiver coupled to the processor and adapted to communicate with a remote device, and the processor is adapted to control the infusion device by causing the transmitter/receiver to send information about the impact to the remote device.

In some embodiments, the acceleration sensor is an accelerometer. In other embodiments, the acceleration sensor is an impact switch disposed within the housing.

In additional embodiments, the infusion device also includes a memory contained in the housing and coupled to the processor. The memory is adapted to store a predetermined acceleration force corresponding to a physical activity of the person. If the acceleration output signal exceeds the predetermined acceleration force, the processor is adapted to control the infusion device by causing the indicator to notify the person about the physical activity. Alternatively, the processor is adapted to control the infusion device by causing the drive mechanism to alter delivery of the fluid into the person's body from a current delivery rate to a modified delivery rate. In further alternative embodiments, the infusion device also includes a transmitter/receiver coupled to the processor and adapted to communicate with a remote device, and the processor is adapted to control the infusion device by causing the transmitter/receiver to send information about the physical activity to the remote device. In other embodiments, the memory is further adapted to store data about at least one of frequency, duration, and intensity of the physical activity of the person.

In another embodiment of the present invention, an ambulatory medical device such as an external infusion device for infusing fluid into a person from a reservoir comprises a housing adapted to be carried on an exterior of the person's body. The infusion device also includes a drive mechanism contained in the housing and operatively coupled to the reservoir to deliver the fluid from the reservoir into the person's body. The infusion device further includes a processor contained in the housing, and a memory coupled to the processor and adapted to store a predetermined temperature threshold. A thermal sensor is also coupled to the processor and adapted to provide a temperature output signal as a function of temperature in the housing. The processor is adapted to compare the temperature output signal with the predetermined temperature threshold, and to control the infusion device based on the temperature comparison.

In particular embodiments, the infusion device further includes an indicator operatively coupled to the processor and adapted to indicate information to the person about the temperature output signal. In some embodiments, if the temperature output signal exceeds the predetermined temperature threshold, the processor is adapted to control the infusion device by causing the indicator to provide an alarm or a warning to the person about the temperature output signal. For example, the fluid infused into the person's body may be medication, and the predetermined temperature threshold may correspond to a temperature that causes the medication to degrade, so that the alarm or warning may indicate degradation of the medication to the person. In other embodiments, if the temperature output signal is less than the predetermined temperature threshold, the processor is adapted to control the infusion device by causing the indicator to provide an alarm or a warning to the person about the temperature output signal. For example, the infusion device may further include a battery that is adapted to provide power for the infusion device and has a discharge resistance that varies with temperature. The predetermined temperature threshold may correspond to a temperature that causes the discharge resistance of the battery to increase by at least 10 percent, so that the alarm or warning may indicate reduced life of the battery to the person.

In additional embodiments, the infusion device includes a battery adapted to provide power for the infusion device. The processor is adapted to sample the battery at a first sampling frequency to determine remaining power of the battery. If the temperature output signal is less than the predetermined temperature threshold, the processor is further adapted to control the infusion device by altering sampling of the battery from the first sampling frequency to a second sampling frequency.

In further embodiments, the memory is also adapted to store a predetermined force threshold corresponding to a fluid occlusion in the infusion device. If the temperature output signal is less than the predetermined temperature threshold, the processor is adapted to control the infusion device by modifying the predetermined force threshold to provide a modified force threshold.

In yet another embodiment of the present invention, an ambulatory medical device such as an external infusion device comprises a housing adapted to be carried by a person and a processor contained in the housing. The infusion device also includes an indicator operatively coupled to the processor and adapted to indicate information about the infusion device to the person. A memory is coupled to the processor and adapted to store a predetermined humidity threshold. The infusion device further includes a humidity sensor coupled to the processor and adapted to provide a humidity output signal as a function of humidity in or around the housing. The processor is adapted to compare the humidity output signal with the predetermined humidity threshold, and to control the infusion device based on the humidity comparison.

In particular embodiments, if the humidity output signal exceeds the predetermined humidity threshold, the processor is adapted to control the infusion device by causing the indicator to provide an alarm or a warning to the person about the humidity output signal. For example, the predetermined humidity threshold may correspond to entry of water into the housing, and the indicator is adapted to provide the alarm or warning to the person about the entry of water into the housing. In other embodiments, if the humidity output signal is less than the predetermined humidity threshold, the processor is adapted to control the infusion device by causing the indicator to provide an alarm or a warning to the person about the humidity output signal. For example, the predetermined humidity threshold may correspond to a humidity level that causes the infusion device to be susceptible to damage due to static electricity, and the indicator is adapted to provide the alarm or warning to the person about the static electricity.

There are additional aspects to the present invention. It should therefore be understood that the preceding is merely a brief summary of some embodiments and aspects of the present inventions. Additional embodiments and aspects of the present inventions are referenced below. It should further be understood that numerous changes to the disclosed embodiments can be made without departing from the spirit or scope of the invention. The preceding summary therefore is not meant to limit the scope of the invention. Rather, the scope of the invention is to be determined by appended claims and their equivalents.

DETAILED DESCRIPTION OF THE INVENTION

Figure 1:
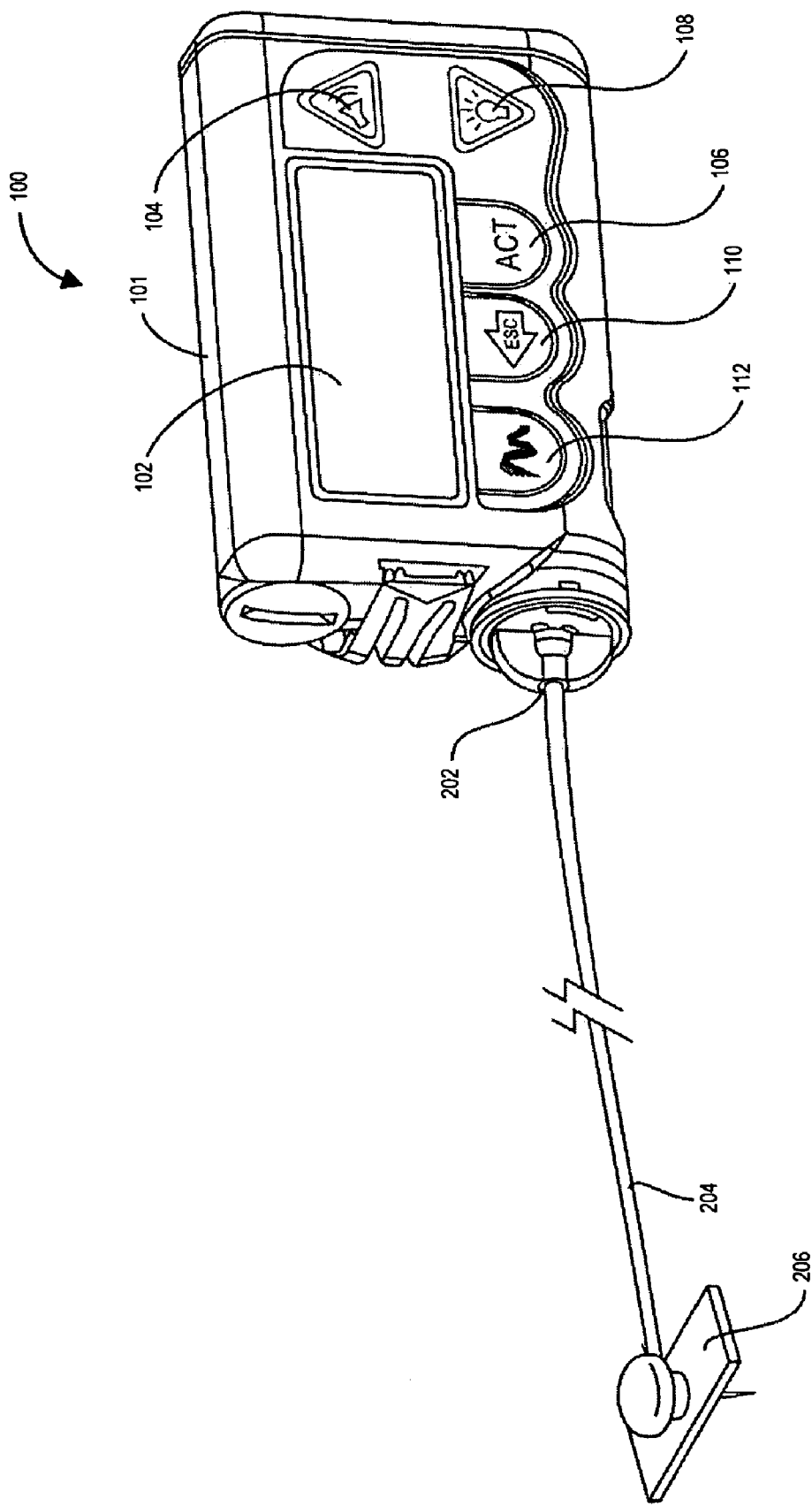
FIG. 1 is a perspective view of an infusion pump according to an embodiment of the present invention.

In the following description, reference is made to the accompanying drawings which form a part hereof and which illustrate several embodiments of the present invention. It is understood that other embodiments may be used, and structural and operational changes may be made without departing from the scope of the present invention.

As shown in the drawings for purposes of illustration, the invention is embodied in an ambulatory medical device that includes acceleration, thermal, and/or humidity sensors for detecting acceleration, temperature, and/or humidity conditions in or around the medical device. In response to detected conditions, the medical device may alter operation of the medical device, provide alarm or text messages to the user, and/or transmit data about the detected conditions to another device or system. In one embodiment, the medical device is a drug delivery system, such as an external infusion pump for delivering insulin into the body of a user. However, in alternative embodiments, the medical device may be other drug delivery systems for delivering other fluids into the body of the user, such as medication other than insulin (e.g., HIV drugs, drugs to treat pulmonary hypertension, iron chelation drugs, pain medications, and anti-cancer treatments), chemicals, enzymes, antigens, hormones, vitamins, or the like. In other alternative embodiments, the medical device may be a patient monitoring system, such as a continuous glucose monitoring system for determining glucose levels in the blood or other bodily fluids of the user. In further alternative embodiments, the medical device may be other patient monitoring systems (e.g., pulse rate monitors, electrocardiogram monitors, and the like, such as the Holter monitor) for determining the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like.

One example of an ambulatory medical device is the external infusion pump 100 shown in FIG. 1. The pump 100 includes a housing 101 that contains an electronics compartment (not shown), including a processor (not shown) for running programs and controlling the pump 100. The pump 100 may be programmed by a care provider, such as a physician or trained medical personnel, or by the user. To program the pump 100, an individual utilizes a display 102 and a keypad of buttons 104, 106, 108, 110, and 112 located on the housing 101 to access and/or modify control parameters and data for the pump 100. The display 102 provides information regarding program parameters, delivery profiles, pump operation, alarms, warnings, statuses, or the like. In the embodiment shown in FIG. 1, the pump 100 has five buttons or keys including an Up-Arrow key 104, an ACT (activate) key 106, a Down-Arrow key 108, an ESC (escape) Key 110, and an Express Bolus key 112. In alternative embodiments, the pump 100 may utilize more or less keys or have different key arrangements than those illustrated in the figure. The pump 100 uses the control parameters to calculate and issue commands that affect the rate and/or frequency that the pump 100 delivers fluid, preferably medication such as insulin, through a fitting 202 and flexible tubing 204, and into an infusion set 206 that is adhered to the body of the user.

Figure 2:
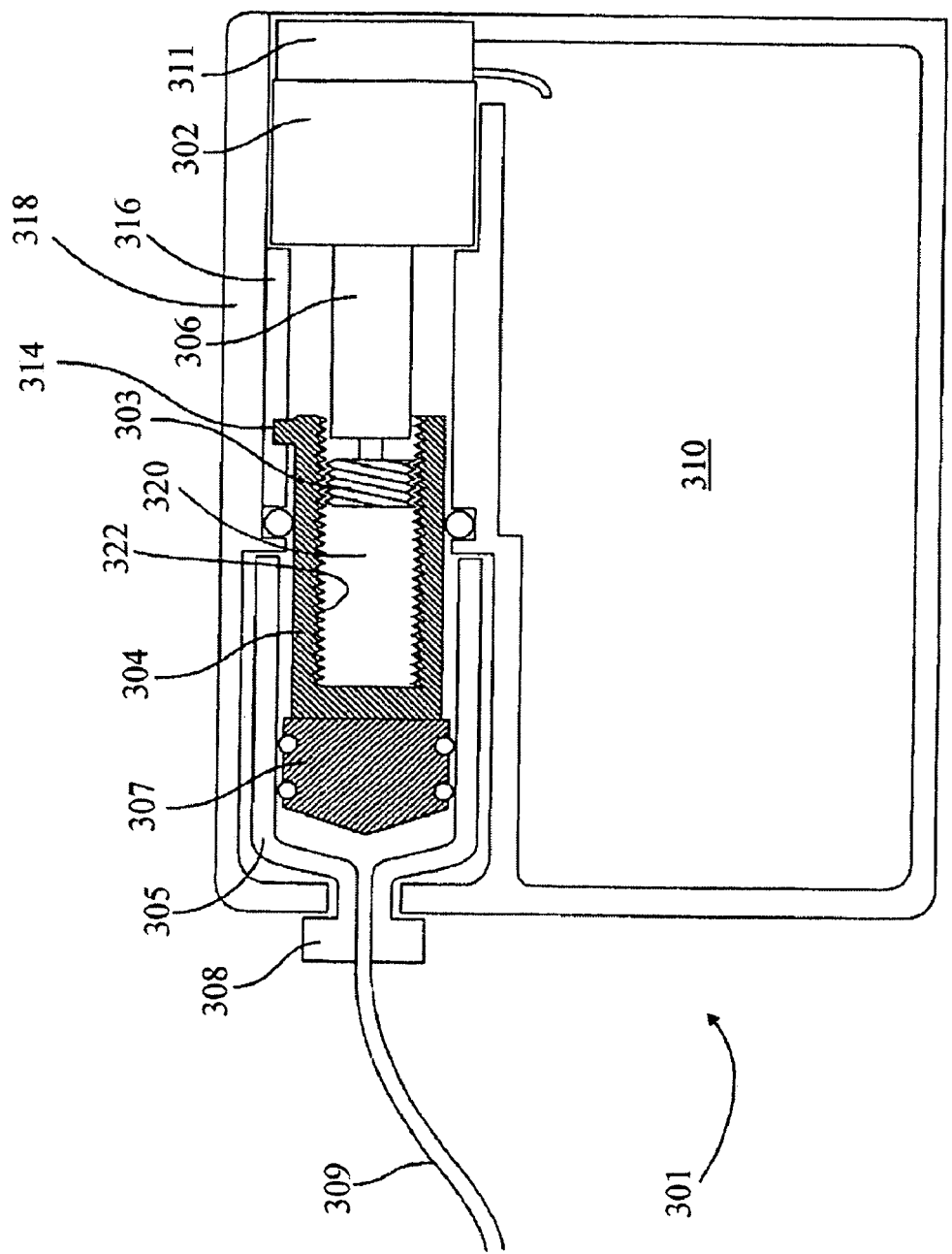
FIG. 2 is a side plan, cut-away view of an infusion pump drive system in accordance with an embodiment of the present invention.

FIG. 2 illustrates a drive system for an infusion pump 301 according to an embodiment of the present invention. The pump 301 includes a housing 318 that contains an electronics compartment 310. The electronics compartment 310 houses a power supply (not shown) for providing power to operate the pump 301, and system electronics for the pump 301, including a processor (not shown) for running programs and controlling the pump 301. The housing 318 of the pump 301 also contains a drive mechanism including a motor 302, gear box 306, drive screw 303, slide 304, stopper 307, and reservoir 305, which are generally concentrically aligned. The motor 302 rotates the drive screw 303 via the gear box 306. The drive screw 303 has external threads, which engage internal threads 322 on a cylindrical bore 320 running most of the length of the slide 304. Thus, the rotational torque of the drive screw 303 is translated into axial force on the slide 304. The slide 304 further includes one or more tabs 314 that fit within one or more slots 316 in the housing 318 to prevent the slide 304 from rotating with respect to the housing 318. As the drive screw 303 rotates, the slide 304 is forced to travel along its axis. The slide 304 is in removable contact with the stopper 307 within the reservoir 305. As the slide 304 advances into the reservoir 305, the stopper 307 is displaced forcing fluid out of the reservoir 305, through a fitting 308 and tubing 309, and into an infusion set (not shown) attached to the body of the user.

A sensor 311 is positioned between the motor 302 and the housing 318 to detect forces translated from fluid pressure within the reservoir 305 through the stopper 307, slide 304, drive screw 303, and the gear box 306 to the motor 302. The sensor 311 provides a range of measurements based on the detected forces. However, because the infusion pump 301 can be carried by users who engage in a variety of physical activities and travel, the pump 301 can be subjected to various environmental changes that do not always result in occlusions, but nevertheless can either adversely affect performance of the pump 301 or indicate a need to vary operation of the pump 301 due to changing medication needs of the user. Therefore, the pump 301 also includes acceleration, thermal, and/or humidity sensors (not shown) which, as explained in greater detail below, can detect acceleration, temperature, and/or humidity conditions in or around the pump 301, and in response to the detected conditions, the pump 301 may alter its operation, provide an alarm or text message to the user, or transmit data to another device.

Figure 3:
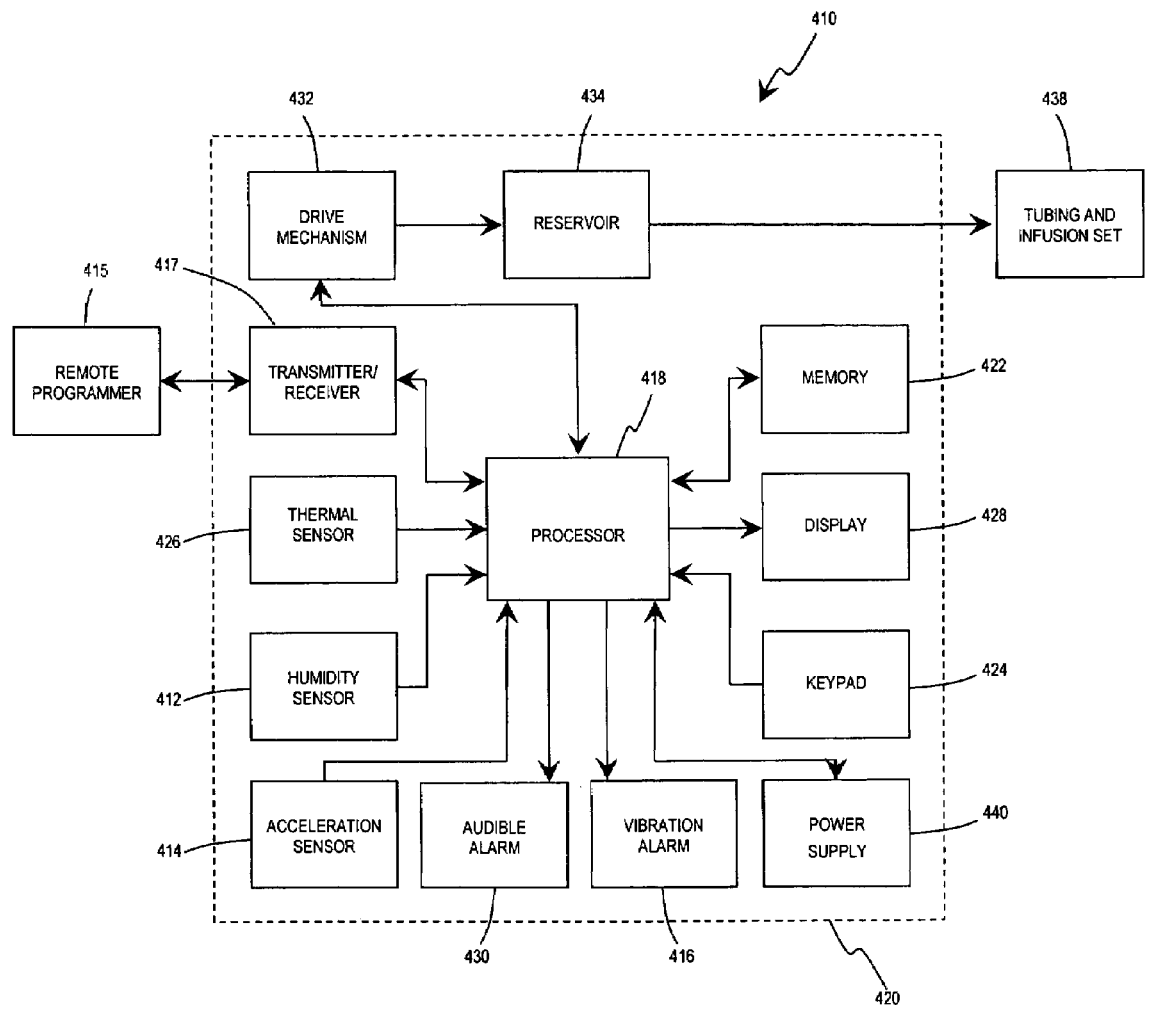
FIG. 3 is a simplified block diagram of an infusion pump and system in accordance with an embodiment of the present invention.

FIG. 3 illustrates one hardware and software environment in which certain embodiments of the present invention may be implemented. In one embodiment, an ambulatory medical device is a drug delivery system, such as an external infusion pump, for regulating the delivery of medication such as insulin into the body of a user. Examples of the infusion pump may be of the type shown and described in U.S. Pat. Nos. 4,562,751; 4,678,408; 4,685,903; 5,080,653; 5,097,122; 5,505,709; 6,248,093; 6,362,591; 6,554,798; 6,555,986; and 6,752,787, which are herein incorporated by reference.

As shown in FIG. 3, the infusion pump 410 includes a housing 420 that contains a processor 418 adapted to control the pump 410. The processor 418 is coupled to a drive mechanism 432, which is connected to a reservoir 434 containing fluid. The drive mechanism 432 causes the fluid to be delivered from the reservoir 434, and then into a body of a user through tubing and an infusion set 438. The processor 418 is also coupled to an internal memory device 422 that stores programs, historical data, user-defined information, and parameters. In one embodiment, the memory 422 is a flash memory and SRAM; however, in alternative embodiments, the memory 422 may comprise other devices, such as ROM, DRAM, RAM, EPROM, dynamic storage such as other flash memory, or an energy efficient hard-drive.

The infusion pump 410 is programmed by a user input device, such as a keypad 424 mounted on the exterior of the housing 420 and coupled to the processor 418. An individual, such as a care provider or a user, presses keys on the keypad 424 to display and scroll through information, call up menus, select menu items, select control parameters, change control parameters (change values or settings), enter information, turn on a backlight, and the like. Feedback from the infusion pump 410 on status or programming changes is provided to the individual on an indication device, such as visually on a display 428, audibly through an audible alarm 430 (e.g., piezo buzzer, annuciator, speaker, or the like), and/or tactilely through a vibration alarm 416. The individual may activate or deactivate the audible alarm 430 and/or the vibration alarm 416 by accessing control parameters on the pump 410. Feedback from the infusion pump 410 may include signals that notify the individual of modifications to the control parameters, announce that the infusion pump 410 is about to initiate a particular operation, indicate a mode of operation, provide a warning (for instance to indicate a low fluid level in the reservoir or low battery power), present an alarm (such as from a timer or a clock), present an error message to indicate a malfunction of the system (such as an occlusion that restricts the delivery of the fluid, a software error, or the like), request input, confirm that communication has been established, and the like. Alarms and warnings may start out at a low level and escalate until acknowledged by the user. In particular embodiments, the alarm intensity changes over time. If the individual does not respond to the alarm, the alarm may change tone, change volume, increase the vibration amplitude or frequency, project a brighter light or a different color light, flash, flash at a different frequency, and the like. In alternative embodiments, the intensity may vary up or down, or alternatively, the intensity may be constant. In other alternative embodiments, the intensity may change by activating different alarm types over time.

In further alternative embodiments, the keypad 424 may be omitted, and the display 428 may be used as a touch screen input device. In yet other alternative embodiments, the infusion pump 410 may be programmed by commands received from a remote programmer 415 (e.g., PDA, programmer dedicated to communication with the infusion pump 410, or the like) through a transmitter/receiver 417 that is coupled to the processor 418. The remote programmer 415 may be used to program the infusion pump 410 in addition to the keypad 424, display 428, audible alarm 430, and/or vibration alarm 416. Alternatively, the keypad 424, display 428, audible alarm 430, and/or vibration alarm 416 may be omitted, and all programming may be handled by the remote programmer 415. In other alternative embodiments, the infusion pump 410 may be programmed through an interface, such as a cable or communication station, using a computer or the like.

In the illustrated embodiment, a power supply 440, such as a battery, provides the power to operate the infusion pump 410. In particular embodiments, the power supply is one or more replaceable AAA batteries. Energy storage devices such as capacitors, backup batteries, or the like provide temporary power to maintain the memory during power supply replacement. In alternative embodiments, the power supply is one or more button batteries, zinc air batteries, alkaline batteries, lithium batteries, lithium silver oxide batteries, AA batteries, or the like. In still further alternative embodiments, the power supply is rechargeable.

The infusion pump 410 may also allow the user to transfer or download information (e.g., infusion pump history data, sensor data, data from other medical devices, updates to programs, or the like) between the memory 422 of the infusion pump 410 and an external device, such as the remote programmer 415, a computer, another medical device (e.g., blood glucose meter, glucose monitor), or the like. For example, information may be transferred to and/or from the infusion pump 410 through an interface, such as a cable or communication station, to a computer, or alternatively, over the Internet to a remote server, for storage. Alternatively, information may be transferred to and/or from the transmitter/receiver 417 of the infusion pump 410 via a wireless or wired connection to a transmitter/receiver in an external device, such as an external communication link, computer, the remote programmer 415, or the like. The transmitter/receiver 417 of the infusion pump 410 may communicate with external devices using radio frequencies; however, alternative embodiments may use optical, infrared (IR), ultrasonic frequencies, magnetic effects, electrical cables, or the like.

In other alternative embodiments, the infusion pump may include separate durable and disposable housing portions that selectively engage and disengage from each other. The durable housing portion may include the electronics (e.g., processor, memory, and the like) and drive mechanism, and the disposable housing portion may include the reservoir and/or other components that may be disposed of after a prescribed period. Such an infusion pump may be of the type shown and described in U.S. Provisional Application Ser. No. 60/678,290 filed May 6, 2005 and entitled "Infusion Device and Method with Disposable Portion," U.S. application Ser. No. 11/211,095 filed Aug. 23, 2005 and entitled "Infusion Device and Method with Disposable Portion," and U.S. application Ser. No. 11/210,467 filed Aug. 23, 2005 and entitled "Infusion Device and Method with Drive Device in Infusion Device and Method with Drive Device in Separable Durable Housing," all of which are herein incorporated by reference. Such an infusion pump may also be of the type shown and described in U.S. Provisional Application Ser. No. 60/839,821 filed Aug. 23, 2006 and entitled "Systems and Methods Allowing for Reservoir Filling and Infusion Medium Delivery," U.S. Provisional Application Ser. No. 60/839,822 filed Aug. 23, 2006 and entitled "Infusion Medium Delivery Device and Method with Drive Device for Driving Plunger in Reservoir," U.S. Provisional Application Ser. No. 60/839,832 filed Aug. 23, 2006 and entitled "Infusion Medium Delivery Device and Method with Compressible or Curved Reservoir or Conduit," U.S. Provisional Application Ser. No. 60/839,840 filed Aug. 23, 2006 and entitled "Infusion Medium Delivery System, Device and Method with Needle Inserter and Needle Inserter Device and Method," and U.S. Provisional Application Ser. No. 60/839,741 filed Aug. 23, 2006 and entitled "Infusion Pumps and Methods and Delivery Devices and Methods with Same," all of which are herein incorporated by reference.

As previously discussed, ambulatory medical devices, including drug delivery systems such as an external infusion pump, may encounter various environmental changes that could adversely affect performance. For example, a pump can be damaged if dropped or bumped onto a hard object or surface such as a floor, doorway, counter or desk. If the pump is dropped or bumped with sufficient force, it may become damaged to an extent that it cannot adequately perform its intended functions. The tubing, infusion set, or reservoir may become damaged such that medication leaks out and is not delivered to the user. Also, the pump housing may become cracked, or the electronics or power supply or drive mechanism contained within the pump may become damaged by the impact. If the pump lacks the ability to detect and alarm for this condition, the user may not receive the expected medication and may experience adverse effects such as hyperglycemia. Additionally, if the pump becomes damaged due to an impact, it would be useful to indicate this condition to the user, such as by an alarm (display, audio or vibratory), thus notifying him or her of the need to check the pump for damage. Furthermore, if the pump is dropped or bumped with sufficient force along the axis of the reservoir, unintended medication delivery may occur. The user may unexpectedly receive medication, and as a result, experience hypoglycemia. It would be useful to notify the user of the impact so that the user could take preventative measures to avoid hypoglycemia.

Ambulatory medical devices may also come into contact with external fluids such as water or cleaning agents. For example, some external infusion pumps are labeled for use in water. If the pump housing becomes cracked due to an impact, fluid may be able to enter the pump, and as a result, the pump may no longer function properly. Again, it would be useful to notify the user of this potential condition, thus permitting a self-check of the pump or notification of the manufacturer or a repair facility for assistance.

Therefore, the infusion pump 410 further includes an acceleration sensor 414, a thermal sensor 426, and a humidity sensor 412. The acceleration, thermal, and humidity sensors 414, 426, and 412 are coupled to and communicate with the processor 418. For example, based on data from the acceleration, thermal, and/or humidity sensors 414, 426, and 412, the processor 418 may: (1) cause the drive mechanism 432 to alter the fluid delivery rate, (2) activate the display 428, audible alarm 430, and/or vibration alarm 416 to provide alarms or warnings to the user, and/or (3) utilize the transmitter/receiver 417 to send data to another device, such as the remote programmer 415 or other remote devices or systems via remote data communication network(s). Examples of communication between the pump 410 (or other medical device) and a remote device or system via a remote data communication network may be of the type shown and described in U.S. application Ser. No. 11/414,160 filed Apr. 28, 2006 and entitled "Remote Monitoring for Networked Fluid Infusion Systems," which is herein incorporated by reference. For example, the pump 410 may transmit information (e.g., warnings, alarms, notifications) based on data from the acceleration, thermal, and/or humidity sensors 414, 426, and 412 to a remote device carried by the user's caregiver or physician via a computer network, pager network, cellular telecommunication network, satellite communication network, or the like. Additionally, the memory 422 is adapted to store values associated with the outputs of the acceleration sensor 414, the thermal sensor 426, and the humidity sensor 412, as well as values associated with predetermined acceleration forces, temperatures, and humidity levels.

In alternative embodiments of the present invention, the ambulatory medical device may be other drug delivery systems for delivering other fluids into the body of the user, such as medication other than insulin (e.g., HIV drugs, drugs to treat pulmonary hypertension, iron chelation drugs, pain medications, and anti-cancer treatments), chemicals, enzymes, antigens, hormones, vitamins, or the like. In other alternative embodiments, the medical device may be a patient monitoring system, such as a continuous glucose monitoring system, for obtaining an indication of glucose levels in the blood or other fluids in the body of a user. Examples of the continuous glucose monitoring system may be of the type shown and described in U.S. Pat. Nos. 6,248,067; 6,418,332; 6,424,847; 6,809,653; and 6,895,263, which are herein incorporated by reference. In further alternative embodiments, the medical device may be other patient monitoring systems (e.g., pulse rate monitors, electrocardiogram monitors, and the like, such as the Holter monitor) for determining the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like. Such medical devices may include acceleration, thermal, and/or humidity sensors similar to the sensors 414, 426, and 412.

In particular embodiments, an acceleration sensor 414 is included within an ambulatory medical device such as the infusion pump 410 and is used as an indicator of potential damage to the pump 410 due to an impact. In one embodiment, the acceleration sensor 414 is an accelerometer which provides a signal that is proportional to the acceleration (or deceleration) forces (i.e., the rate of change of velocity with respect to time) to which the pump 410 is subjected. The processor 418 within the pump 410 monitors the signal from the accelerometer for a value larger than a predetermined or programmed threshold stored in memory 422, and if the accelerometer signal reaches that threshold, the processor 418 causes an alarm or warning to be provided to the user visually on the display 428, audibly by the audible alarm 430, and/or tactilely with the vibration alarm 416. The acceleration threshold may be determined by testing or other methods to be the acceleration which may potentially cause damage to any part of the pump 410.

Accelerometers typically have one or more axes of sensitivity. In the simplest form, the accelerometer can have a single axis of sensitivity. Therefore, the signal generated from the accelerometer will be the vector sum of accelerations along that axis. This property can be beneficial since the accelerometer can be mounted such that its axis of sensitivity is aligned with the direction of most concern within the ambulatory medical device.

If there is concern for damage to the medical device along multiple directions (axes), then multiple, single-axis accelerometers can be used. Alternatively, a single acceleration sensor may have multiple axes of sensitivity and detect acceleration in a plurality of directions. One example of such an acceleration sensor is described in U.S. Pat. No. 5,833,713. Again, this sensor can be mounted in the medical device in an orientation that monitors acceleration signals in the desired directions.

If there is concern for damage to the medical device due to impact in any direction, then a 3-axis accelerometer can be used, such as one manufactured by Entran Devices, Inc., Fairfield, N.J. A 3-axis orthogonal accelerometer can be mounted as a discrete component within the medical device, such as within the housing, attached to a mechanical component, or directly on a printed circuit board. For example, such an accelerometer could be mounted within the housing 420 of the pump 410, attached to a component of the drive mechanism 432, or directly on the circuit board that includes the processor 418 or other electronic components.

Furthermore, if it is desirable to have different levels of sensitivity along multiple axes, then an accelerometer with discrete axes of sensitivity can be mounted along each of those axes (i.e. orthogonal or not orthogonal) and monitored and processed independently. For example, the acceleration sensor 414 within the pump 410 can be an orthogonal 3-axis accelerometer and monitor the signals from each axis independently. If, in this example, it is desired to have different levels of sensitivity along the axis of the reservoir 434, the axis perpendicular to the display 428, and the corresponding orthogonal axis, then the accelerometer can be mounted so that each of the three orthogonal sensor axes is aligned with one of those directions. Thus, each of these axes can be monitored independently and produce acceleration signals corresponding to impacts in those directions.

Varying acceleration threshold levels can be programmed into the pump 410 for each of these axes or combination of axes to produce the appropriate alarm or warning messages. For example, a light impact generating a relatively low acceleration level can result in a warning to the user to look for potential damage to his/her pump 410, whereas a hard impact generating a relatively high acceleration level can result in an alarm and instructions for the user to call the manufacturer and return the pump 410 for analysis. The processor 418 may activate the display 428, audible alarm 430, and/or vibration alarm 416 to provide alarms or warnings to the user. For example, the pump 410 can alarm and instruct the user to investigate damage, such as a leaking infusion set 438 or broken reservoir 434, a cracked pump housing 420 or damage to the power supply 440 or other electronic components. The pump 410 can also instruct the user to perform a self-check, or it can automatically run a self-check to identify damage that may not be visible to the user. Further, the processor 418 may cause the drive mechanism 432 to alter the delivery of fluid to the user or activate the transmitter/receiver 417 to cause data, such as alarms, to be sent to another device, such as the remote programmer 415.

Accelerometers are based on several different technologies, such as piezoelectric, thermal, servo, strain gauge, capacitance, micro electromechanical systems ("MEMS"), and resonance shift. Each of these technologies has different advantages. Piezoelectric ("PE") sensors generate a charge when strained. Since PE sensors generate their own signal, they are referred to as active sensors. However, PE sensors provide only an AC response, and thus, can only detect impacts or shock to the medical device. Such PE sensors are available from several companies including Measurement Specialties, Inc., Fairfield, N.J.

Another class of sensors is referred to as passive sensors, which change some measurable property when strained. For example, a piezoresistive sensor changes its resistance when strained. Piezoresistive sensors provide both an AC and DC response, and thus, can detect both impacts or shock to, as well as slight tilt or movement of, the medical device. However, in order to measure the change in resistance, piezoresistive sensors require a constant power supply. Other examples of passive sensors include capacitive based sensors which measure a change in capacitance when strained, and resonance shift sensors which measure a shift in frequency when loaded or strained.

The choice of sensor technology depends on the available power supply, the need to measure a steady-state (DC) input, and the desired frequency of measurement. In the case of many ambulatory medical devices such as external infusion pumps, the power supply is limited to a battery. In one embodiment of such a medical device, continuous non-DC measurement may be desired. Therefore, a sensor technology that requires very low power to operate is often desirable for such medical devices. Since piezoresistive sensors require a constant power supply to operate, this sensor technology may not be appropriate. However, since piezoelectric sensors are active devices that can generate a signal, less power may be required to operate them, and thus, they may be a more desirable sensor technology for battery-powered, ambulatory medical devices such as external infusion pumps.

Figure 4:
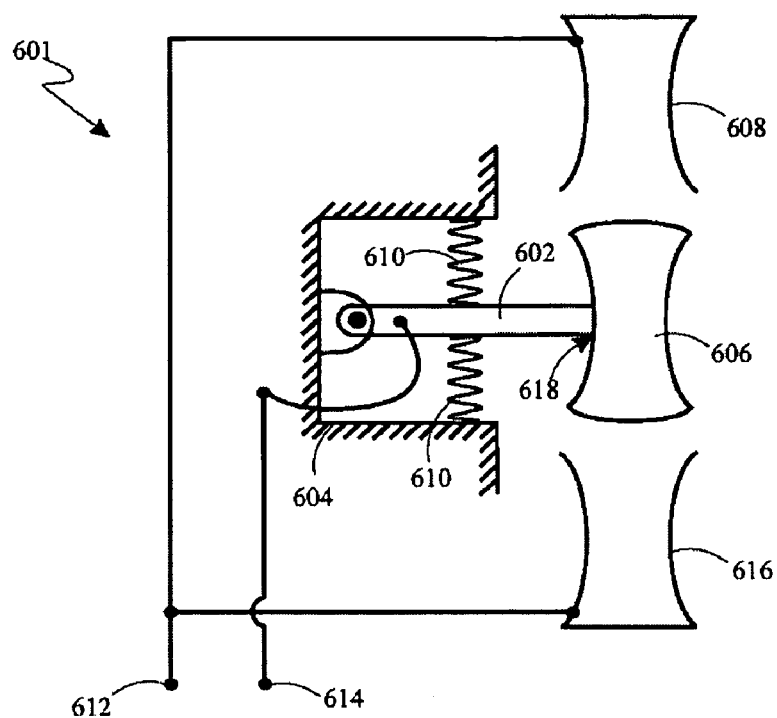
FIG. 4 is a simplified schematic diagram of an impact switch in accordance with one embodiment of the invention.

In alternative embodiments, the acceleration sensor 414 incorporated into an ambulatory medical device such as the infusion pump 410 may be an impact or acceleration switch, which provides an "on" or "off" output signal when its seismic mass is subjected to a predetermined level of acceleration. FIG. 4 shows a simplistic representation of an impact switch 601 with an "on" or "off" state. The switch 601 includes a seismic mass 618 comprised of an electrically conductive arm 602 and an electrically conductive plug 606. The arm 602 is pivotably coupled to a housing 604 of the medical device, and the plug 606 is mounted on the free end of the arm 602. The plug 606 is electrically coupled to the arm 602, and the arm 602 is electrically coupled to an electrical output 614. In yet another embodiment, the plug 606 may be omitted, and the seismic mass 618 may simply include the arm 602 having a free end and adapted to be held by a latch mechanism.

The switch 601 also includes a first electrically conductive latch 608 and a second electrically conductive latch 616, which are adapted to releasably secure the plug 606 and are electrically coupled to an electrical input 612. In the illustrated embodiment, the first and second latches 608 and 616 are latch springs having a concave-shaped cross section. The plug 606 has a complementary concave-shaped cross-section that allows the plug 606 to mate with either of the latch springs 608 or 616. However, in other embodiments, the latches 608 and 616 and the plug 606 may have alternative geometries or latching mechanisms.

In the illustrated embodiment, the switch 601 further includes two opposed springs 610 that bias the arm 602 such that the plug 606 is in a spaced-apart relationship between the first latch 608 and the second latch 616. In one embodiment, the springs 610 may be coil springs; however, in alternative embodiments, the springs 610 may be other biasing elements, such as leaf springs or the like.

Referring back to FIG. 4, when the medical device is subjected to an acceleration force of a predetermined magnitude and direction along an axis of sensitivity of the switch 601, the arm 602 will pivot toward one of the latches 608 or 616, and the plug 606 will be releasably secured by that latch 608 or 616. As a result, a circuit between the electrical input 612 and the electrical output 614 will be closed, thereby providing an output signal that indicates the medical device has been subjected to an acceleration force of the predetermined magnitude and direction along the axis of sensitivity of the medical device.

One advantage of an impact switch that can maintain its "on/off" state relates to the operation of the electronics within a battery-operated, ambulatory medical device such as an external infusion pump. It is common for certain sub-systems requiring higher power (e.g., microprocessor, power supply, motor, or measurement system) to shut down when not in use, and then "wake-up" only during scheduled times to perform their operation or function, in order to extend battery life. Because the switch can maintain its change of state (i.e., the electrical connection between the electrical input and electrical output) due to an impact, the medical device does not have to continuously monitor for a signal from the impact switch. Thus, the medical device can shut down certain system electronics when not in use, and wait until the next time the system electronics "wake-up" to check for a signal from the switch. As described above, the appropriate alarms or warnings can be provided to the user upon detecting a signal from the impact switch. Alternatively, the switch can cause the drive system to be shut down so that the drive system cannot be inadvertently activated due to the impact.

Figure 5:
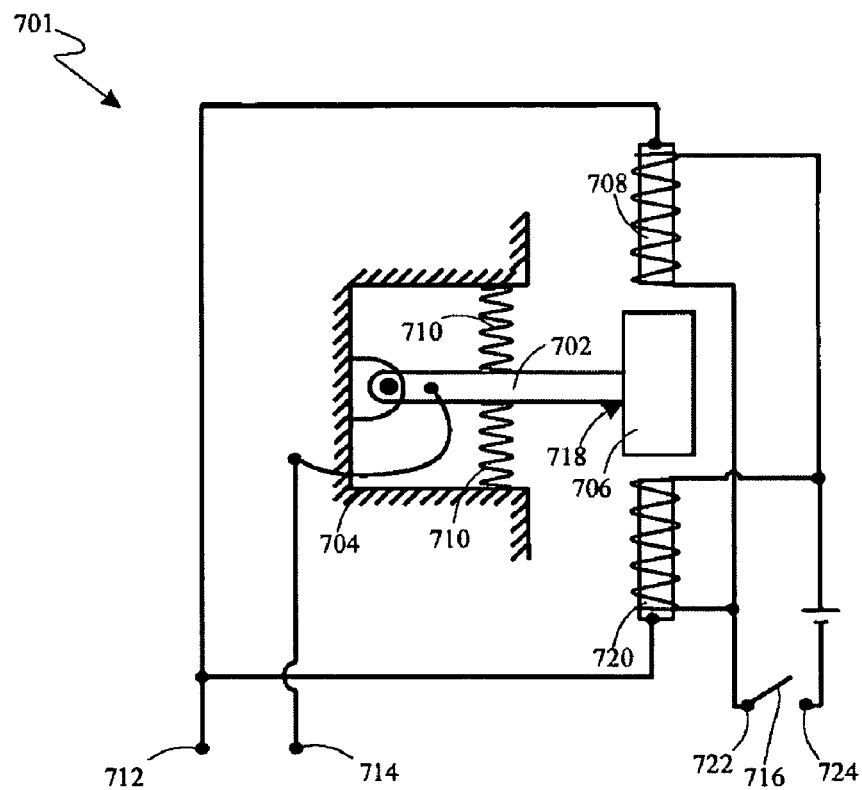
FIG. 5 is a simplified schematic diagram of an impact switch in accordance with an alternative embodiment of the invention.

FIG. 5 shows an alternative embodiment of an impact switch 701 that can maintain its "on/off" state. The switch 701 includes a seismic mass 718 comprised of an electrically conductive arm 702 and an electrically conductive contact member 706. The arm 702 is pivotably coupled to a housing 704 of the medical device, and the contact member 706 is mounted on the free end of the arm 702. The arm 702 and the contact member 706 are electrically coupled to one another and to a switch electrical output 714. In another embodiment, the contact member 706 may be omitted, and the seismic mass 718 may simply include the arm 702 having a free end and adapted to abut and be held in position by an electromagnet.

The switch 701 also includes first and second electromagnets 708 and 720, which are adapted to generate magnetic fields that individually have sufficient strength to releasably hold the contact member 706, at least a portion of which is constructed of a ferromagnetic material. The first and second electromagnets 708 and 720 are also electrically coupled to a switch electrical input 712. Power to the electromagnets 708 and 720 for generating the magnetic fields is provided via a magnet electrical input 722 and a magnet electrical output 724. A reset switch 716 electrically connects the magnet electrical input 722 to the magnet electrical output 724 when the switch 716 is closed, thus shunting the electricity flow from the electromagnets 708 and 720 and causing the magnetic field to collapse.

In the illustrated embodiment, the switch 701 further includes two opposed springs 710 that bias the arm 702 such that the contact member 706 is in a spaced-apart relationship between the first and second electromagnets 708, 720. In one embodiment, the springs 710 may be coil springs; however, in alternative embodiments, the springs 710 may be other biasing elements, such as leaf springs or the like.

Referring back to FIG. 5, when the switch 701 is subjected to an acceleration force of a predetermined magnitude and direction along an axis of sensitivity of the switch 701, the arm 702 will pivot toward one of the electromagnets 708 or 720, and the contact member 706 will abut the electromagnet 708 or 720 and be releasably held in position by its magnetic field. As a result, a circuit between the switch electrical input 712 and the switch electrical output 714 is closed, thereby providing an output signal that indicates the medical device has been subjected to an acceleration force of the predetermined magnitude and direction along the axis of sensitivity of the medical device. When it is desired to reset the impact switch 701, the reset switch 716 is closed, thus collapsing the magnetic fields and releasing the contact member 706 to return to its initial position between the electromagnets 708 and 720.

As with the switch 601 of FIG. 4, this switch 701 of FIG. 5 also will latch its condition upon experiencing a predetermined acceleration force. However, this type of switch 701 may be better suited for reset following acknowledgement of an alarm since electromagnets 708 and 720 are used to hold the contact member 706. The use of a switch, such as the reset switch 716 of FIG. 5, to reset the impact switch 701 after an alarm may be more convenient in some applications than the use of a mechanical release mechanism to release the latch plug 606 from one of the latches 608 or 616 in the embodiment of FIG. 4.

Figure 7:
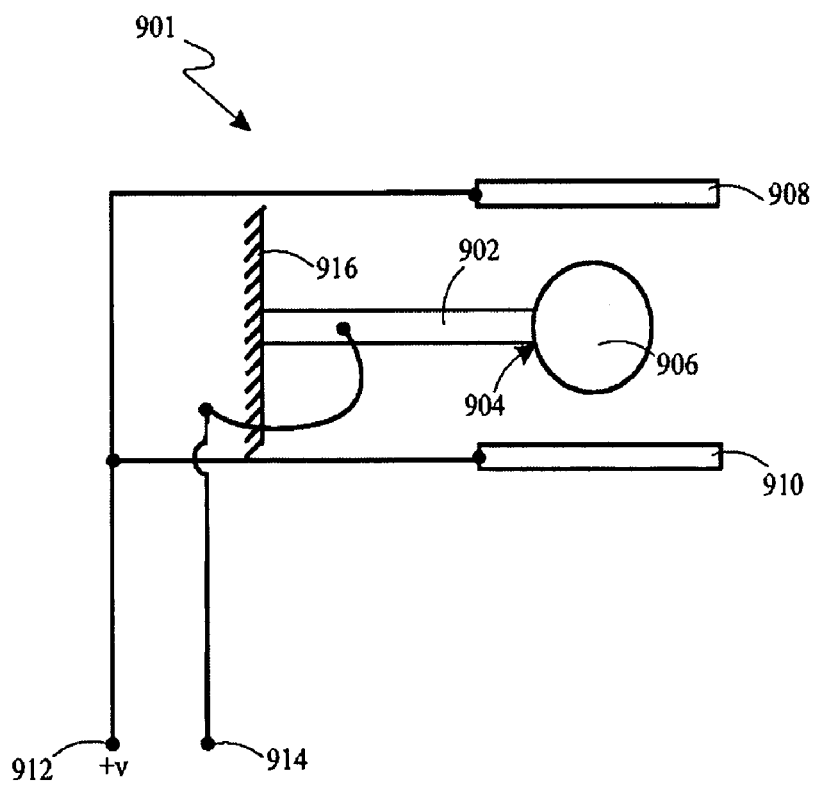
FIG. 7 is a simplified schematic diagram of an impact switch in accordance with an alternative embodiment of the invention.

FIG. 7 illustrates another embodiment of an impact switch 901 that can be incorporated as an acceleration sensor 414 into an ambulatory medical device such as an external infusion pump 410. The impact switch 901 includes a seismic mass 904 comprised of an electrically conductive arm member 902 and an electrically conductive impact head 906. The arm 902 has one end rigidly coupled to a housing 916 of the medical device. Alternatively, the arm 902 may be coupled to electronics (not shown) contained within the housing of the medical device. In the illustrated embodiment, the impact head 906 is mounted on the free end of the arm 902 and is electrically coupled to the arm 902. The arm 902 is constructed of a material that permits resilient deflection and is electrically coupled to an electrical output 914. For example, the arm 902 can be constructed of stainless steel or beryllium copper, or other materials having the desired resiliency and electrical conductivity.

The switch 901 also includes two electrically conductive contacts 908 and 910, which are fixedly mounted adjacent to the impact head 906 and are electrically coupled to an electrical input 912. Thus, the impact head 906 is in a spaced-apart relationship between the contacts 908 and 910 when no acceleration force acts on the medical device.

When the medical device is subjected to an acceleration force of a predetermined magnitude and direction along an axis of sensitivity of the switch 901, the arm 902 will deflect toward one of the contacts 908 or 910, and the head 906 will briefly touch that contact 908 or 910 before returning to its equilibrium position. When this occurs, the electrical circuit between the electrical input 912 and the electrical output 914 is momentarily closed, thus producing a voltage spike or pulse at the electrical output 914. System electronics monitor the output 914 for such a voltage pulse, and provide an appropriate alarm or other indication as described above when such a pulse is detected.

Figure 6:
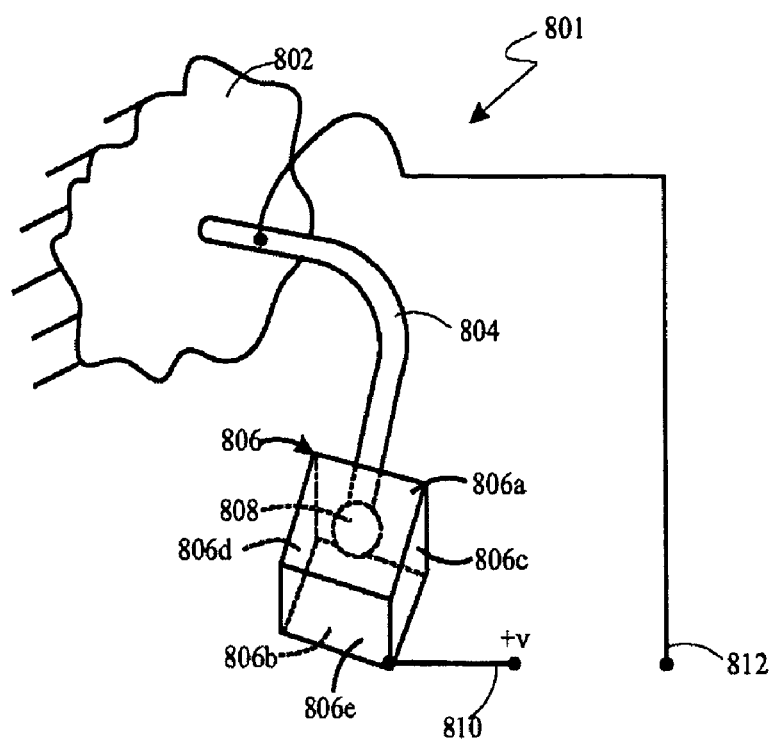
FIG. 6 is a simplified schematic diagram of an impact switch in accordance with an alternative embodiment of the invention.

FIG. 6 shows yet another embodiment of an impact switch 801, which employs a principle similar to that of the switch 901 of FIG. 7. However, the switch 801 of FIG. 6 can provide an output signal as a function of predetermined acceleration forces along two, three or more axes of sensitivity of the switch 801. Additionally, the switch 801 can have the same or different levels of sensitivity (i.e., respond to different acceleration forces) along each axis of sensitivity of the switch 801. The switch 801 includes a seismic mass comprised of a hook-shaped arm member 804 rigidly coupled to a housing 802 of the medical device and an electrically conductive impact head 808 secured to the free end of the arm 804. The arm 804 is electrically conductive and is electrically coupled to an electrical output 812.

The arm 804 is constructed of a material that allows for resilient deflection, and due to its hook shape, is adapted for deflection along a plurality of imaginary lines of motion in three dimensions. For example, the arm 804 can be constructed of stainless steel, beryllium copper, or other materials having the desired resiliency and electrical conductivity. Alternatively, the arm can be made of nonconductive material having the desired resiliency, such as plastic, and a flexible wire having the desired electrical conductivity can be integrated with the arm. Each of the imaginary lines of motion defines an imaginary plane. Thus, a plurality of imaginary planes are defined, some of which have a relationship other than being parallel to one another, including planes that are generally orthogonal to one another in three dimensions. In the illustrated embodiment, the arm 804 has a hook or bend with a curvature of approximately 90 degrees. In other embodiments, the curvature may be less or more than 90 degrees, such as, for example, a curvature of between 45 degrees and 135 degrees.

Five electrically conductive contact surfaces 806a-806e are fixedly mounted to form a conductive, generally box-shaped enclosure 806 having an open end. The enclosure 806 generally surrounds both the impact head 808 as well as a portion of the free end of the arm 804. All of the contact surfaces 806a-806e are electrically coupled to an electrical input 810. The impact head 808 is in a spaced apart relationship with each of the surfaces 806a-806e when no acceleration force acts on the medical device.

When an acceleration force of a predetermined magnitude and direction acts on the medical device, the arm 804 deflects and the impact head 808 briefly touches one of the contact surfaces 806a-806e before returning to the equilibrium position. When this occurs, the electrical circuit between the electrical input 810 and the electrical output 812 is momentarily completed, thus producing a voltage spike or pulse at the electrical output 812. System electronics monitor the output 812 for such a voltage pulse, and provide an appropriate alarm or other indication as described above when such a pulse is detected.

Although the embodiment of FIG. 6 involves five generally planar-shaped contact surfaces that form a generally box-shaped enclosure, other embodiments may include a greater or lesser number of contact surfaces having different shapes that may or may not form an enclosure. For example, one embodiment may include only two planar-shaped contact surfaces that are oriented generally orthogonal to one another. On the other hand, other embodiments may include a plurality of contact surfaces that form any polyhedron-shaped enclosure having geometries other than the box-shaped enclosure of FIG. 6 or that form a spherical or cylindrical-shaped enclosure.

With respect to the embodiments of both FIGS. 6 and 7, various impact acceleration set points can be established by varying the length of the arm 804 or 902, the curvature of the bend in the arm 804 in FIG. 6, the cross-sectional shape of the arm 804 or 902, the material from which the arm 804 or 902 is constructed, the density of the material from which the impact head 808 or 906 is constructed, and the distance between the impact head 808 or 906 and the contact surface 806a-e or 908 and 910 at equilibrium (i.e. when no acceleration force is being applied to the switch 801 or 901). In other alternative embodiments, the impact head 808 or 906 may be omitted, and the arm 804 or 902 may come into contact with the contact surfaces 806a-e or 908 and 910 to close the electrical circuit and produce an output signal at the electrical output 812 or 912.

As described above, an acceleration sensor such as an accelerometer or impact switch may be used to detect and report potential damage to an ambulatory medical device due to shock or impact. Additionally, an accelerometer can be used to detect physical activities of the user, and then the user's therapy can be adjusted or operation of the medical device can otherwise be altered in response to the detected activity of the user, as will be described below.

The accelerometers described above can be carried or worn by individuals to monitor their physical activities, including exercise. Such physical activity generally results in an accelerometer frequency output in the range of 10-60 Hz, up to 100 Hz. Typically, each type of physical activity in which the user engages (e.g., running, walking, sitting, etc.) generates a different frequency that can be detected and identified. Thus, in other embodiments of the present invention, an ambulatory medical device such as the external infusion pump 410 may include an acceleration sensor 414 such as one or more accelerometers that provide signals as a function of a plurality of acceleration forces acting on the pump 410 and corresponding to physical activity of the user. In one embodiment, the pump 410 may determine that the user is engaging in physical activity if the output signal of the acceleration sensor 414 exceeds a predetermined acceleration force that is known to correspond to such physical activity. In other embodiments, the pump 410 may determine that the user is engaging in physical activity based on a trace or pattern of output signals from the acceleration sensor 414. For example, running may result in one trace or pattern of varying magnitudes of output signals from the acceleration sensor 414, while walking may result in another trace or pattern of varying magnitudes of output signals from the acceleration sensor 414. The pump monitors the physical activity of the user and responds accordingly by providing messages or alarms to the user (i.e., visually on the display 428, audibly by the speaker 430, and/or tactilely via the vibration alarm 416), adjusting the delivery of medication to the user, or otherwise altering the operation of the pump 410.

For example, some users require less medication, such as insulin, during periods of intense exercise and/or for certain periods of time after such exercise. The acceleration sensor 414 incorporated into the pump 410 may be used to detect such exercise or other physical activity by the user. In response to the detected exercise or physical activity, the pump 410 can notify the user to decrease the medication delivery rate. In alternative embodiments, the pump 410 can automatically decrease the medication delivery rate. Moreover, the pump 410 can apply a time delay between detecting the commencement of exercise and decreasing the medication delivery rate. The time delay may be a predetermined period of time for the pump 410 (e.g., 5 minutes), or alternatively, the user may program the length of the delay. Furthermore, the pump 410 may vary the length of the delay based on the duration and/or intensity of the exercise. In still other embodiments, the pump 410 may change the nocturnal delivery rate (i.e., the delivery rate when the user is sleeping) in response to detected exercise earlier in the day.

In particular embodiments, the pump 410 allows the user to program the amount of decrease in the medication delivery rate during and/or after the period of exercise. For example, the user can enter a percentage decrease of the current delivery rate to be used when exercise is detected. Alternatively, the user can set a specified delivery rate to be used when exercise is detected. The delivery rate during and/or after exercise may be any rate that is lower than the delivery rate used when not exercising, including no medication delivery during exercise.

In other embodiments, the pump 410 may correlate the detected duration and intensity of physical activity to caloric burn. This correlation may be performed utilizing known algorithms and data correlating exercise to caloric burn that are preprogrammed into the pump 410 and/or input into the pump 410 by the user or caregiver. Based on the estimated caloric burn, the pump 410 may notify the user of possible hypoglycemia if the caloric burn is high, or alternatively, suggest more exercise for the user if the caloric burn is low. The pump 410 may also modify the medication delivery rate based on the estimated caloric burn. For example, the pump 410 may decrease the medication delivery rate if the caloric burn is high.

In alternative embodiments, the pump 410 may deliver medications or fluids other than insulin. As a result, in some embodiments, the user may desire more medication or other fluids during exercise. Thus, in response to the detected exercise or physical activity by the user, the delivery rate may be increased in a manner similar to that described above for decreasing the delivery rate. For example, the pump may deliver medications or other fluids such as nutrients, vitamins, minerals, steroids, anabolic drugs, glucose, salts, sources of energy, painkillers, drugs to enhance oxygen uptake, fluids for hydration, or the like.

In particular embodiments, the acceleration sensor 414 incorporated into the pump 410 may also be used to detect the cessation of exercise or physical activity by the user. In response to the detected cessation of exercise or physical activity, the pump 410 can remind the user to return to the normal, programmed delivery rate. In alternative embodiments, the pump 410 can automatically return to the normal, programmed delivery rate. Additionally, the pump may apply a time delay between detecting the cessation of exercise and returning to the normal, programmed delivery rate.

For some users, the length of the delay between ending exercise and returning to the normal, programmed delivery rate may be dependent on the duration of the exercise. For example, if the user has exercised for 30 minutes or less, the pump 410 may delay for a period of 5 minutes after the user has stopped exercising, and then return to the normal, programmed delivery rate. In another example, if the user has exercised for more than 30 minutes, the pump 410 may delay for a period of 10 minutes after the user has stopped exercising, and then return to the normal, programmed delivery rate. Other time periods of delay or exercise may be used. In alternative embodiments, the user may program the length of the delay between detecting the cessation of exercise and returning to the normal, programmed delivery rate.

In further alternative embodiments, the pump 410 may change the delivery rate gradually from the normal programmed delivery rate to the exercise delivery rate, and from the exercise delivery rate to the normal programmed delivery rate. These gradual changes in rates or dosages can occur over a period of time in a generally linear manner, a generally quadratic manner, a generally exponential manner, or a generally logarithmic manner.

In other embodiments, exercise characteristics, such as frequency, duration, and/or intensity, may be detected by the acceleration sensor 414 incorporated into the ambulatory medical device such as the infusion pump 410, and then stored in a history file or database. In one embodiment, the exercise characteristics may be downloaded from the transmitter/receiver 417 via a wired or wireless connection to a computer, PDA, the Internet, or the like, where an exercise history file or database is maintained. Alternatively, the exercise history file may be stored and maintained in the memory 422 of the pump 410. The history file is analyzed to determine if the user's exercise routine has changed, and if so, the user is notified to re-evaluate his or her medication delivery rate.

For example, some users may require more or less medication, such as insulin, depending on their exercise routine. For users who have significantly increased their exercise routine and improved their physical conditioning, the amount of insulin required per gram of carbohydrate ingested (i.e., carbohydrate ratio) and/or the amount of insulin required to lower their blood glucose level a certain number of units (i.e., insulin sensitivity) may decrease. On the other hand, for users who have significantly decreased their exercise routine and lost some physical conditioning, the amount of insulin required per gram of carbohydrate ingested (i.e., carbohydrate ratio) and/or the amount of insulin required to lower their blood glucose level a certain number of units (i.e., insulin sensitivity) may increase.

In some embodiments, the user may be notified when his or her exercise routine has changed throughout a period of three months. Alternatively, users can be notified when their exercise routine has changed for longer or shorter periods of time. For example, some users with diabetes may require a different amount of insulin when they are ill compared to when they are healthy. Thus, if such a user is ill and cannot exercise, then after just 2 or 3 days, the pump can notify the user to re-evaluate his/her carbohydrate ratio and/or insulin sensitivity.

In particular embodiments, the exercise history file may be maintained and analyzed on a device other than the pump 410, such as a computer, PDA, the Internet, or the like. The user may then be notified that his/her exercise routine has changed and/or to re-evaluate his/her medication delivery rate by email, while operating a computer program, while communicating with a web site, or the like. Alternatively, the user can receive this notification from the user's glucose meter or monitoring system, PDA, cell phone, or the like. In further alternative embodiments, this notification can be transmitted to the transmitter/receiver 417, and then provided to the user by the pump 410 visually on the display 428, audibly by the audible alarm 430, and/or tactilely via the vibration alarm 416. In other embodiments, the exercise history file may be maintained and analyzed on the pump 410. The pump 410 then notifies the user that the user's exercise routine has changed and/or to re-evaluate the user's medication delivery rate visually on the display 428, audibly by the audible alarm 430, and/or tactilely via the vibration alarm 416. In alternative embodiments, the transmitter/receiver 417 may be utilized to communicate this notification to a device other than the infusion pump 410 so that the user can receive this notification as described above, such as by email, while operating a computer program, while communicating with a web site, or the like. Alternatively, the user can receive this notification from the user's glucose meter or monitoring system, PDA, cell phone, or the like.

In further alternative embodiments, sensing devices other than an acceleration sensor 414 incorporated into the infusion pump 410 may be used to detect exercise, such as for example, a respiratory rate measuring device, a blood glucose monitor, a heart rate measurement device, a blood oxygen sensor, a body temperature sensor, or the like. These sensing devices can communicate with the pump 410 via the transmitter/receiver 417, and the pump 410 can maintain and analyze the exercise history file and/or modify the medication delivery rate. In other alternative embodiments, these sensing devices can communicate with a device external to the pump 410 (e.g., computer, PDA, the Internet), which stores and analyzes the exercise history file. If the pump 410 or device external to the pump 410 (e.g., computer, PDA, the Internet) determines that the user's exercise routine has changed, the user can be notified of such change and/or to re-evaluate his/her medication delivery rate by the pump 410 or other external device as described above.

In addition to acceleration, other environmental conditions can adversely affect the performance of ambulatory medical devices such as the infusion pump 410. For example, temperature extremes can affect both performance of the infusion pump 410 as well as certain medications, such as insulin. Thus, an ambulatory medical device such as the infusion pump 410 may also include a temperature or thermal sensor 426, which allows the pump 410 to notify the user when the pump 410 is exposed to varying or extreme temperatures (hot or cold). Temperature sensing can be used, for example, to estimate the effect of temperature on the performance of the pump 410 itself, the pump's power supply 440 such as a battery, and/or degradation of insulin or other medication. The thermal sensor 426 may be any of the known thermal sensors, including, for example, thermoresistors (thermistors), thermocouples, thermal flow rate sensors, resistance temperature detectors ("RTDs"), platinum resistors, diode temperature sensors, silicon transistor thermometers, integrated temperature transducers, PTAT circuits, thermopiles, pyroelectric thermometers, quartz thermometers, and the like.

RTD's operate on the principle that the electrical resistance of many metals, such as platinum, aluminum and copper, or the like will increase over a certain range of temperatures. A fine wire of metal is wound on a core to obtain a high level of resistance or is patterned as a thin film on a substrate. The varying resistance is then measured as a function of temperature.

A thermistor sensor also operates on the principle of varying electrical resistances as a function of temperature. However, these devices are made from various nonmetallic conductors (e.g., metal oxides and silicon) and can offer the advantage of higher thermal coefficients of resistance and greater sensitivities ($\Delta R/\Delta T$). Moreover, some types of thermistors provide increasing electrical resistance as temperature increases, whereas other types provide decreasing resistance.

A thermocouple sensor consists of two dissimilar metals that are bonded together by welding or other means. The bimetallic junction develops a small voltage that varies with temperature. Thermocouples are relatively inexpensive and provide moderately accurate and consistent measurements. However, one disadvantage is that they produce very small output voltages which are comparable to the voltages developed at the junctions formed where the thermocouple wire is connected to other components. This must be compensated for in the associated circuitry.

Many temperature sensor integrated circuit devices operate on the principle that at a constant current bias, the voltage drop across a silicon P—N diode junction can vary with temperature. Because the P—N junction is the basic building block of diodes, transistors, and ICs, temperature sensing can be incorporated at a relatively low cost.

There are various uses for a temperature or thermal sensor 426 in an ambulatory medical device such as the infusion pump 410. In one embodiment, the infusion pump 410 uses the temperature sensor 426 for warning purposes. In extreme environments, medication such as insulin can degrade and become less effective. Also, electronic components of the pump 410 may malfunction (e.g., the display 428 may go blank). The thermal sensor 426 is used to measure or detect temperature conditions to which the pump 410 is subjected, and in response to the detected temperature, the pump 410 can notify the user of potential problems due to the temperature before they occur (e.g., insulin degradation, electronics malfunction). Additionally, if the thermal sensor 426 detects a sufficiently high or low temperature, problems such as insulin degradation may have already occurred. Thus, the pump 410 can provide the user with an alarm to notify the user of the insulin degradation.

In operation, the thermal sensor 426 provides an output signal as a function of the temperature in the housing 420. The processor 418 converts the output signal to a value, and compares that value with a predetermined temperature value stored in the memory 422 that is associated with a predetermined temperature. If the temperature measured by the thermal sensor 426 exceeds the predetermined temperature, the processor 418 may provide an alarm to the user (i.e., tactilely via the vibration alarm 416, audibly by the audible alarm 430, and/or visually on the display 428) to indicate that the pump 410 has been subjected to extremely high temperatures, and as a result, to check the pump (e.g., whether insulin degradation has occurred, the display has malfunctioned).

Additionally, in cold environments, there may be a higher occurrence of medication flow stoppage due to the reduced viscosity of some medications such as insulin. The lower viscosity fluid requires a higher force to deliver the fluid from the reservoir, through the tubing, and into the infusion set adhered to the patient. However, this higher delivery force can be more likely to trigger a false occlusion alarm as compared with pump operations at warmer temperatures. Accordingly, in another embodiment of the present invention, for an ambulatory medical device such as the infusion pump 301 which utilizes a force sensor 311 to detect occlusions, the programmed occlusion alarm limits are made dependent on the measured temperatures to which the pump 301 is subjected. When the temperature decreases, the pump occlusion alarm limit is increased accordingly.

In operation, the memory 422 stores a predetermined temperature value associated with a predetermined temperature and a predetermined force threshold value associated with a predetermined force threshold corresponding to a fluid occlusion. The thermal sensor 426 provides an output signal as a function of the temperature in the housing 420. The processor 418 converts the output signal to a value, and compares that value with the predetermined temperature value. If the temperature measured by the thermal sensor 426 is less than the predetermined temperature, the processor 418 alters the predetermined force threshold value to provide a modified force threshold value. In other words, the force threshold corresponding to an occlusion is changed. Subsequently, if a measured force (as measured, for example, by the force sensor 311) exceeds the modified force threshold value, the processor 418 provides an alarm to the user (i.e., visually on the display 428, audibly by the audible alarm 430, and/or tactilely via the vibration alarm 416) to indicate the occlusion.

In other embodiments, temperature data is used to modify a delivery pulse of the pump. For example, in some ambulatory medical devices such as the infusion pump 410, friction within the drive mechanism 432 and/or reservoir 434 is often dependent on the temperature at which the pump 410 is operating. As temperature decreases, friction increases, and as a result, more energy is required by the drive mechanism 432 to deliver fluid out of the reservoir 434. Therefore, the thermal sensor 426 can measure the temperature within the pump housing 420. The processor 418 compares the measured temperature with a predetermined temperature stored in the memory 422. If the measured temperature is below the predetermined temperature, the processor 418 increases the delivery pulse, for example, by increasing the duration or the amount of energy in the delivery pulse.

In yet another embodiment, temperature data is used as an indicator of reduced battery life. For example, in some ambulatory medical devices such as the infusion pump 410, alkaline-manganese dioxide batteries can be used as the power supply 440. Battery performance is often dependent on the temperature at which the battery is operating. As temperature decreases, the discharge resistance of the battery increases, thereby reducing the battery's life. Therefore, the thermal sensor 426 can measure the temperature within the pump housing 420. The processor 418 compares the measured temperature with a predetermined temperature stored in the memory 422. For example, the predetermined temperature may be a temperature that causes a battery discharge resistance increase of 10, 15, 25, 50 percent or some other percentage. If the measured temperature is below the predetermined temperature, the pump 410 provides an alarm to the user, indicating that battery life may be reduced due to the temperature to which the pump 410 is subjected.

Additionally, in other embodiments, an ambulatory medical device such as the infusion pump 410 uses temperature data to modify battery measurement algorithms. In one embodiment, when the temperature decreases, the measurement frequency of the power supply 440 such as the battery may be increased to ensure that there is adequate power for effective operation of the pump 410. For example, in the infusion pump 410, a battery measurement may be taken every hour. Since the act of taking this measurement requires power, it can be important to minimize the frequency of battery measurements. On the other hand, if there are external conditions that effectively reduce the battery performance, such as lower temperatures, it may be desirable to modify the pump 410 to take battery measurements differently, possibly more frequently, so that appropriate low battery and dead battery conditions can be detected earlier than otherwise.

Thus, the processor 418 samples the output voltage of the battery 440 at a first sampling frequency. The thermal sensor 426 provides an output signal as a function of the temperature in the housing 420. The processor 418 converts the output signal to a value and compares that value with a predetermined temperature value stored in the memory 422 corresponding to a predetermined temperature. If the temperature measured by the thermal sensor 426 is less than the predetermined temperature, the processor 418 alters the battery voltage sampling from the first sampling frequency to a second sampling frequency in accordance with this comparison.

Humidity is yet another environmental variable that can affect performance of an ambulatory medical device such as the infusion pump 410. In one embodiment, the humidity sensor 412 is incorporated within the infusion pump 410, and provides an output signal as a function of humidity levels in the housing 420. Alternatively, the humidity sensor 412 can be disposed to provide an output signal as a function of humidity levels external to the housing 420.

The processor 418 converts the output signal from the humidity sensor to a value, and compares that value with a predetermined value stored in the memory 422 that is associated with a predetermined humidity level. Based on the comparison, the processor 418 then provides a warning or alarm to the user (i.e., visually on the display 428, audibly by the audible alarm 430, and/or tactilely via the vibration alarm 416). The humidity sensor 412 may be any of the known humidity sensors, including capacitive humidity sensors, resistive humidity sensors, and thermal conductivity humidity sensors.

Capacitive humidity sensors consist of a substrate on which a thin film of polymer or metal oxide is deposited between two conductive electrodes. The sensing surface is coated with a porous metal electrode to protect it from contamination and exposure to condensation. The change in the dielectric constant of a capacitive humidity sensor is proportional to the relative humidity of the surrounding environment.

Resistive humidity sensors measure the change in electrical impedance of a hygroscopic medium such as a conductive polymer, salt, or treated substrate. The impedance change is typically inversely proportional to the humidity level. Resistive sensors frequently consist of noble metal electrodes deposited on a substrate. The substrate can be coated with a salt or conductive polymer. When it is dissolved or suspended in a liquid binder, it functions as a vehicle to evenly coat the sensor.

Thermal conductivity humidity sensors measure the absolute humidity by quantifying the difference in the thermal conductivity between dry air and air containing water vapor. They usually consist of two thermistor elements in a bridge circuit—one is encapsulated in a gas, such as dry nitrogen, and the other is exposed to the environment. When current is passed through the thermistors, resistive heating increases their temperature. The heat dissipated from the encapsulated thermistor is greater than the exposed thermistor due to the difference in the thermal conductivity of the water vapor as compared to dry nitrogen. Since the heat dissipated yields different operating temperatures, the difference in resistance of the thermistors is proportional to the humidity.

In particular embodiments, humidity measurements from within an ambulatory medical device such as the infusion pump 410 are used to detect a breach in the pump's watertight integrity. The humidity sensor 412 may measure the humidity level within the housing 420 of the pump 410, and the processor 418 may compare the measured humidity with a predetermined humidity level stored in the memory 422. For example, the predetermined humidity level may be a very high humidity level (e.g., greater than 90%, 80%, or some other percentage) within the housing 420 of the pump 410 that may indicate possible water intrusion into the pump 410 due to a damaged housing 420. If the measured humidity exceeds the predetermined humidity level, the pump 410 notifies the user and indicates the necessity to perform some self-test or investigation, or to contact the manufacturer for service. This notification can be provided tactilely via the vibration alarm 416, audibly by the audible alarm 430, and/or visually on the display 428. Alternatively, the processor 418 can activate the transmitter/receiver 417, which can send the humidity level information to an external device for analysis or notification to the user.

Although some ambulatory medical devices are designed to be resistant to the effects of static electricity, it nevertheless is possible that high levels of static discharge can cause such a device to alarm. A significant environmental parameter affecting the generation of static electricity is humidity. The effects of static electricity increase with a decrease in humidity. Therefore, in another embodiment, the humidity sensor 412 in an ambulatory medical device such as the infusion pump 410 can measure humidity external to the pump 410, and the user can then be notified of high humidity conditions. Alternatively, humidity measured by the humidity sensor 412 from within the pump 410 can also be used. However, there likely will be a time lag between a change in external humidity and the detection of such a change by the humidity sensor 412 that measures internal humidity.

Thus, there is disclosed an ambulatory medical device that is adapted for carrying by a person, preferably by external attachment to the person's body. The ambulatory medical device has acceleration, thermal and/or humidity sensors which, along with system electronics, control the device by, among other things, altering the operation of the device, providing an alarm or text message to the user, and/or transmitting data to another device.

While the description above refers to particular embodiments of the present invention, it will be understood that many modifications may be made without departing from the spirit thereof. The claims are intended to cover such modifications as would fall within the true scope and spirit of the present invention. The presently disclosed embodiments are therefore to be considered in all respects as illustrative and not restrictive, the scope of the invention being indicated by the claims rather than the foregoing description, and all changes which come within the meaning and range of equivalency of the claims are therefore intended to be embraced therein.

What is claimed is:

1. An external infusion device for infusing fluid into a person from a reservoir, comprising:
    a housing adapted to be carried on an exterior of the person;
    a drive mechanism contained in the housing and operatively coupled to the reservoir to deliver fluid from the reservoir into the person;
    a processor contained in the housing;
    an indicator operatively coupled to the processor and adapted to provide at least one of a visual indication, an audible indication, or a tactile indication to indicate information about the infusion device to the person; and
    an acceleration sensor coupled to the processor and adapted to provide an acceleration output signal as a function of acceleration forces acting on the housing, wherein the acceleration sensor is an impact switch disposed within the housing, the impact switch comprising:
        an electrical input and an electrical output,
        an electrically conductive seismic mass having an anchored end and a free end, the mass being electrically coupled to the electrical output, the mass being coupled to the housing at the anchored end and adapted for resilient deflection in a first closing contact direction, and
        a first electrically conductive contact fixedly mounted adjacent to the mass, the first contact being electrically coupled to the electrical input,
        wherein the mass is adapted to deflect in the first closing contact direction from a first position to a second position, touch the first contact, and return from the second position to the first position such that a circuit between the electrical input and the electrical output is closed to provide the acceleration output signal when a first predetermined acceleration force acts on the housing;

wherein the processor is adapted to control the infusion device in accordance with the acceleration output signal.

2. The external infusion device of claim 1, further comprising a memory contained in the housing and coupled to the processor, wherein the memory is adapted to store a predetermined acceleration threshold corresponding to an impact on the housing.

3. The external infusion device of claim 2, wherein if the acceleration output signal exceeds the predetermined acceleration threshold, the processor is adapted to control the infusion device by causing the indicator to provide an alarm or a warning to the person.

4. The external infusion device of claim 2, wherein if the acceleration output signal exceeds the predetermined acceleration threshold, the processor is adapted to control the infusion device by causing the drive mechanism to alter delivery of the fluid into the person.

5. The external infusion device of claim 2, further comprising a transmitter/receiver contained in the housing and coupled to the processor, wherein the transmitter/receiver is adapted to communicate with a remote device, and further wherein if the acceleration output signal exceeds the predetermined acceleration threshold, the processor is adapted to control the infusion device by causing the transmitter/receiver to send information about the impact to the remote device.

6. The external infusion device of claim 1, wherein the conductive seismic mass comprises:
an electrically conductive arm member having a proximate end and a distal end, the arm member being coupled to the housing at the proximate end and adapted for resilient deflection in the first closing contact direction; and
an electrically conductive impact head mounted on the distal end of the arm member, the impact head being electrically coupled to the arm member,
wherein the arm member is adapted to deflect from the first position to the second position, the impact head is adapted to touch the first contact, and the arm member is adapted to return from the second position to the first position when the first predetermined acceleration force acts on the housing.

7. The external infusion device of claim 1, wherein the impact switch further comprises:
a second electrically conductive contact fixedly mounted adjacent to the seismic mass, the second contact being electrically coupled to the electrical input,
wherein the mass is further adapted for resilient deflection in a second closing contact direction, and
wherein the mass is adapted to deflect in the second closing contact direction from the first position to a third position, touch the second contact, and return from the third position to the first position such that a circuit between the electrical input and the electrical output is closed to provide the acceleration output signal when a second predetermined acceleration force acts on the housing.

8. The external infusion device of claim 1, wherein the processor is further adapted to determine whether the person is engaging in a physical activity based on the acceleration output signal.

9. The external infusion device of claim 8, further comprising a memory contained in the housing and coupled to the processor, wherein the memory is adapted to store a predetermined acceleration force corresponding to a physical activity of the person, and the processor determines that the person is engaging in the physical activity if the acceleration output signal exceeds the predetermined acceleration force.

10. The external infusion device of claim 8, further comprising a memory contained in the housing and coupled to the processor, wherein the memory is adapted to store a pattern of acceleration forces corresponding to a physical activity of the person, and the processor determines that the person is engaging in the physical activity if the acceleration output signal corresponds to the pattern of acceleration forces.

11. The external infusion device of claim 8, wherein if the processor determines that the person is engaging in a physical activity, the processor is adapted to control the infusion device by causing the indicator to notify the person about the physical activity.

12. The external infusion device of claim 8, further comprising a transmitter/receiver contained in the housing and coupled to the processor, wherein the transmitter/receiver is adapted to communicate with a remote device, and further wherein if the processor determines that the person is engaging in a physical activity, the processor is adapted to control the infusion device by causing the transmitter/receiver to send information about the physical activity of the person to the remote device.

13. The external infusion device of claim 12, wherein the information includes data about at least one of frequency, duration, and intensity of the physical activity of the person.

14. The external infusion device of claim 8, further comprising a memory contained in the housing and coupled to the processor, wherein the memory is further adapted to store data about at least one of frequency, duration, and intensity of the physical activity of the person.

15. The external infusion device of claim 8, wherein if the processor determines that the person is engaging in a physical activity, the processor is adapted to control the infusion device by causing the drive mechanism to alter delivery of the fluid into the person from a current delivery rate to a modified delivery rate.

16. The external infusion device of claim 15, wherein the processor is adapted to control the infusion device by causing the drive mechanism to automatically alter delivery of the fluid into the person from the current delivery rate to the modified delivery rate.

17. The external infusion device of claim 16, further comprising an input device coupled to the processor and adapted to receive input from the person about the modified delivery rate, wherein the processor is adapted to control the infusion device by causing the drive mechanism to automatically alter delivery of the fluid into the person from the current delivery rate to the modified delivery rate based on the input from the person.

18. The external infusion device of claim 15, further comprising an input device coupled to the processor and adapted to receive input from the person associated with the modified delivery rate, wherein the processor is adapted to control the infusion device by causing the drive mechanism to alter delivery of the fluid into the person from the current delivery rate to the modified delivery rate in response to the input by the person.

19. The external infusion device of claim 15, wherein the processor is adapted to control the infusion device by applying a time delay between determining that the person is engaging in the physical activity and causing the drive mechanism to alter delivery of the fluid into the person from the current delivery rate to the modified delivery rate.

20. The external infusion device of claim 8, wherein the processor is further adapted to determine whether the person has stopped engaging in the physical activity based on the acceleration output signal.

21. The external infusion device of claim 20, further comprising a memory contained in the housing and coupled to the processor, wherein the memory is adapted to store a predetermined acceleration force corresponding to a physical activity of the person, and the processor determines that the person has stopped engaging in the physical activity if the acceleration output signal drops below the predetermined acceleration force.

22. The external infusion device of claim 20, further comprising a memory contained in the housing and coupled to the processor, wherein the memory is adapted to store a pattern of acceleration forces corresponding to a physical activity of the person, and the processor determines that the person has stopped engaging in the physical activity if the acceleration output signal no longer corresponds to the pattern of acceleration forces.

23. The external infusion device of claim 20, wherein if the processor determines that the person has stopped engaging in the physical activity, the processor is adapted to control the infusion device by causing the indicator to notify the person about stopping the physical activity.

24. The external infusion device of claim 20, wherein if the processor determines that the person has stopped engaging in the physical activity, the processor is adapted to control the infusion device by causing the drive mechanism to return delivery of the fluid into the person from the modified delivery rate to the current delivery rate.

25. The external infusion device of claim 24, wherein the processor is adapted to control the infusion device by causing the drive mechanism to automatically return deliver of the fluid into the person from the modified delivery rate to the current delivery rate.

26. The external infusion device of claim 24, further comprising an input device coupled to the processor and adapted to receive input from the person, wherein the processor is adapted to control the infusion device by causing the drive mechanism to return delivery of the fluid into the person from the modified delivery rate to the current delivery rate in response to the input by the person.

27. The external infusion device of claim 24, wherein the processor is adapted to control the infusion device by applying a time delay between determining that the person has stopped engaging in the physical activity and causing the drive mechanism to return delivery of the fluid into the person from the modified delivery rate to the current delivery rate.

28. The external infusion device of claim 8, wherein if the processor determines that the person is engaging in a physical activity, the processor is adapted to control the infusion device by causing the drive mechanism to deliver the fluid into the person at a modified delivery rate after the physical activity while the person is sleeping.

29. An external ambulatory medical device for use on a person's body, comprising:
a housing adapted to be carried on an exterior of the person's body;
a processor contained in the housing;
an indicator operatively coupled to the processor and adapted to provide at least one of a visual indication, an audible indication, or a tactile indication to indicate information about the ambulatory medical device to the person; and
an acceleration sensor coupled to the processor and adapted to provide an acceleration output signal as a function of acceleration forces acting on the housing, wherein the acceleration sensor is an impact switch disposed within the housing, the impact switch comprising:
an electrical input and an electrical output,
an electrically conductive seismic mass having an anchored end and a free end, the mass being electrically coupled to the electrical output, the mass being coupled to the housing at the anchored end and adapted for resilient deflection in a first closing contact direction, and
a first electrically conductive contact fixedly mounted adjacent to the mass, the first contact being electrically coupled to the electrical input,
wherein the mass is adapted to deflect in the first closing contact direction from a first position to a second position, touch the first contact, and return from the second position to the first position such that a circuit between the electrical input and the electrical output is closed to provide the acceleration output signal when a first predetermined acceleration force acts on the housing;
wherein the processor is adapted to control the ambulatory medical device and the indicator is adapted to indicate information about the ambulatory medical device based on the acceleration output signal.

30. The ambulatory medical device of claim 29, wherein the ambulatory medical device is an external infusion pump.

31. The ambulatory medical device of claim 29, wherein the ambulatory medical device is a glucose monitoring device.

32. The ambulatory medical device of claim 29, further comprising a transmitter/receiver contained in the housing and coupled to the processor, wherein the transmitter/receiver is adapted to communicate with a remote device, and further wherein the processor is adapted to control the ambulatory medical device by causing the transmitter/receiver to send information about the ambulatory medical device to the remote device based on the acceleration output signal.

33. The external infusion device of claim 29, wherein the conductive seismic mass comprises:
an electrically conductive arm member having a proximate end and a distal end, the arm member being coupled to the housing at the proximate end and adapted for resilient deflection in the first closing contact direction; and
an electrically conductive impact head mounted on the distal end of the arm member, the impact head being electrically coupled to the arm member,
wherein the arm member is adapted to deflect from the first position to the second position, the impact head is adapted to touch the first contact, and the arm member is adapted to return from the second position to the first position when the first predetermined acceleration force acts on the housing.

34. The external infusion device of claim 29, wherein the impact switch further comprises:
a second electrically conductive contact fixedly mounted adjacent to the seismic mass, the second contact being electrically coupled to the electrical input,
wherein the mass is further adapted for resilient deflection in a second closing contact direction, and
wherein the mass is adapted to deflect in the second closing contact direction from the first position to a third position, touch the second contact, and return from the third position to the first position such that a circuit between the electrical input and the electrical output is closed to provide the acceleration output signal when a second predetermined acceleration force acts on the housing.

* * * * *